United States Patent
Katura et al.

(10) Patent No.: US 11,457,864 B2
(45) Date of Patent: Oct. 4, 2022

(54) SYSTEM, METHOD, AND NON-TRANSITORY COMPUTER READABLE MEDIUM FOR CALCULATING A BRAIN ACTIVITY VALUE OF A USER AND CHANGING A LEVEL OF BRAIN TRAINING CONTENT BEING PERFORMED BY THE USER

(71) Applicant: NeU Corporation, Tokyo (JP)

(72) Inventors: Takusige Katura, Tokyo (JP); Kiyoshi Hasegawa, Tokyo (JP)

(73) Assignee: NEU CORPORATION, Tokyo (JP)

( * ) Notice: Subject to any disclaimer, the term of this patent is extended or adjusted under 35 U.S.C. 154(b) by 250 days.

(21) Appl. No.: 16/336,944

(22) PCT Filed: Sep. 28, 2017

(86) PCT No.: PCT/JP2017/035293
§ 371 (c)(1),
(2) Date: Mar. 27, 2019

(87) PCT Pub. No.: WO2018/062410
PCT Pub. Date: Apr. 5, 2018

(65) Prior Publication Data
US 2019/0261916 A1    Aug. 29, 2019

(30) Foreign Application Priority Data
Sep. 28, 2016 (JP) .............................. JP2016-189987

(51) Int. Cl.
*A61B 5/026*    (2006.01)
*A61B 5/00*    (2006.01)
(Continued)

(52) U.S. Cl.
CPC .............. *A61B 5/486* (2013.01); *A61B 5/026* (2013.01); *A61B 5/6814* (2013.01);
(Continued)

(58) Field of Classification Search
CPC ..... A61B 5/7278; A61B 5/026; A61B 5/0261; A61B 5/486; A61B 5/4064; A61B 5/6814;
(Continued)

(56) References Cited

U.S. PATENT DOCUMENTS 9,911,348 B2 *  3/2018 Merzenich .............. A63F 13/47
10,098,579 B2 * 10/2018 Kang .................... A61B 5/4088
(Continued)

FOREIGN PATENT DOCUMENTS

JP    2004-229948 A    8/2004
JP    2004-294593 A    10/2004
(Continued)

OTHER PUBLICATIONS

Machine translation of WO-2016084834-A1, retrieved from Espacenet on Jan. 25, 2021. (Year: 2016).*
(Continued)

*Primary Examiner* — Navin Natnithithadha
(74) *Attorney, Agent, or Firm* — Mattingly & Malur, PC

(57) ABSTRACT

The present invention provides a system for selecting appropriate brain-training content for each user. The selection system includes: a storage unit for storing detection values obtained by detecting blood flow rates in the head of a user, identifiers for predetermined test content to be performed by the user at the time of the detection of the detection values, and an identifier for the user in association with one another; a calculation unit for calculating, on the basis of the detection values stored in the storage unit, brain-activity values indicating the degree of brain-activity of the user when the predetermined test content is performed by the user; and a selection unit for selecting, on the basis of the brain-activity (Continued)

values calculated by the calculation unit during performance of the predetermined test content, brain-training content to be performed by the user.

6 Claims, 8 Drawing Sheets

(51) Int. Cl.
*G06Q 50/22* (2018.01)
*G06Q 50/10* (2012.01)

(52) U.S. Cl.
CPC .......... *A61B 5/7278* (2013.01); *G06Q 50/10* (2013.01); *G06Q 50/22* (2013.01)

(58) Field of Classification Search
CPC ....... A61B 5/4088; A61B 5/40; A61B 5/4076; A61B 5/16–168; G06F 19/3481; G16H 20/70; G16H 40/63; G06Q 50/22; G06Q 50/10
USPC .......................... 600/504, 544, 545, 300, 301
See application file for complete search history.

(56) References Cited

U.S. PATENT DOCUMENTS

| | | | |
|---|---|---|---|
| 2004/0152060 A1 | 8/2004 | Ando et al. | |
| 2004/0191747 A1 | 9/2004 | Atsumori et al. | |
| 2012/0041330 A1* | 2/2012 | Prichep | A61B 5/291 600/544 |
| 2013/0252215 A1* | 9/2013 | Wu | A61B 5/4088 434/236 |
| 2014/0315169 A1* | 10/2014 | Bohbot | G06T 19/003 434/236 |
| 2015/0010890 A1 | 1/2015 | Kang | |
| 2015/0351655 A1* | 12/2015 | Coleman | G16H 50/20 600/301 |
| 2016/0155355 A1* | 6/2016 | Merzenich | G16H 20/70 434/236 |

FOREIGN PATENT DOCUMENTS

| | | |
|---|---|---|
| JP | 2007-054138 A | 3/2007 |
| JP | 2015-508296 A | 3/2015 |
| WO | 2015/177908 A1 | 11/2015 |
| WO | WO-2016044317 A1 * | 3/2016 ........... A61B 5/6803 |
| WO | WO-2016084834 A1 * | 6/2016 ........... A61B 5/7425 |

OTHER PUBLICATIONS

International Search Report of PCT/JP2017/035293 dated Oct. 24, 2017.
Extended European Search Report received in corresponding European Application No. 17856359.9 dated Feb. 28, 2020.
International Preliminary Report on Patentability received in corresponding International Application No. PCT/JP2017/035293 dated Apr. 11, 2019.

* cited by examiner

FIG.5

| ID | 1001 |
|---|---|
| NAME | YAMADA TARO |
| ADDRESS | IROHA-CHO 1-2-3, CHIYODA-KU, TOKYO |
| DATE OF BIRTH | MAY 18, 1980 |
| HEIGHT | 175 CM |
| WEIGHT | 70 KG |
| DISTINCTION OF SEX | MALE |
| CEREBRAL INFARCTION | NOT AFFECTED |
| DIABETES MELLITUS | AFFECTED |
| . . . | . . . |

T10                    INDIVIDUAL INFORMATION TABLE

FIG.7

| USER ID | NAME OF CHECK CONTENT | | | |
| --- | --- | --- | --- | --- |
| | VISUAL | AUDITORY | SHORT-PERIOD MEMORY | . . . |
| 1001 | 3 | 1 | 5 | . . |
| . . . | . . | . . | . . | . . |

| NAME OF BRAIN TRAINING CONTENT | VISUAL | AUDITORY | SHORT-PERIOD MEMORY | ... |
|---|---|---|---|---|
| CONTENT A | 3 | 0 | 2 | ... |
| CONTENT B | 3 | 0 | 0 | ... |
| CONTENT C | 5 | 2 | 2 | ... |
| CONTENT D | 3 | 0 | 5 | ... |
| ... | ... | ... | ... | ... |

T30

SYSTEM, METHOD, AND NON-TRANSITORY COMPUTER READABLE MEDIUM FOR CALCULATING A BRAIN ACTIVITY VALUE OF A USER AND CHANGING A LEVEL OF BRAIN TRAINING CONTENT BEING PERFORMED BY THE USER

TECHNICAL FIELD

The present invention pertains to a selection system, a selection method, and a selection program.

BACKGROUND ART

A measurement system has hitherto been provided, which acquires information representing brain activity states and includes a head region attaching device called a headset and provided with a near infrared-ray irradiation unit and a near infrared-ray detection unit by detecting variations in bloodflow rate on a brain surface, and by processing detected data in a data processing apparatus.

DOCUMENTS OF PRIOR ARTS

Patent Documents

[Patent Document 1] Japanese Patent Application Laid-Open Publication No. 2004-294593
[Patent Document 2] Japanese Patent Application Publication No. 2007-54138

SUMMARY OF THE INVENTION

Problems to be Solved by the Invention

Measured are brain activity states occurring when a plurality of users (measurement examinees) takes various behaviors. It is considered that the brain activity states when taking a certain behavior are influenced by various natures contained in this behavior and attributes of the user. However, the brain activity states are ever hardly analyzed in consideration of the various natures contained in the behavior and the attributes of the user. The brain activity states are requested to be utilized by analyzing the brain activity states in consideration of the various natures contained in the behavior and the attributes of the user.

There are a variety of brain training contents for activating brain functions in order to keep the brain healthy. The brain functions are exemplified by a verbal memory function, a spatial memory function, a restraining function, and a working memory function. Some of the brain training contents are conducted by solving issues and answering questions on, e.g., an information processing apparatus instanced by a mobile terminal and a personal computer, and by outputting the issues and questions onto a print sheet. The brain functions activated by the user executing the brain training content differ per user. It is therefore required to select a proper brain training content corresponding to the brain activity states of each individual user. There are, however, multiple categories of brain training contents, and it is difficult to select the brain training content suited to the user.

It is an object of the present invention to provide a system to select a proper brain training content per user.

Means for Solving the Problems

The following means are adopted for solving the problems given above.

To be specific, a first aspect is a selection system including:

a storage unit to store a detection value given by detecting a bloodflow rate of a head region of a user, an identifier of a predetermined check content to be performed by the user when detecting the detection value, and an identifier of the user by being associated with each other;

a calculation unit to calculate a brain activity value representing a degree of a brain activity state of the user when making the user perform the predetermined check content, based on the detection value to be stored in the storage unit; and a selection unit to select the brain training content for being performed by the user, based on the brain activity value given when making the user perform the predetermined check content calculated by the calculation unit.

The aspect of the disclosure may be attained by an information processing apparatus that runs a program. In other words, a configuration of the disclosure may be specified as a program for making the information processing apparatus execute processes to be executed respective means in the aspect described above, or as a non-transitory computer readable recording medium recorded with the program. The configuration of the disclosure may also be specified as a method by which the information processing apparatus executes the processes to be executed by the respective means. The configuration of the disclosure may further be specified as a system including the information processing apparatus that executes the processes to be executed by the respective means.

Steps describing the program include, of course, processes to be executed in time series along a written sequence, and, even when not necessarily processed in time series, the processes to be executed in parallel or individually. A part of the steps describing the program may be omitted.

Effect of the Invention

According to a technology of the disclosure, it is feasible to provide an information processing apparatus that analyzes brain activity states measured by a user.

BRIEF DESCRIPTION OF THE DRAWINGS

FIG. 5 is a diagram illustrating an example of an individual information table.
FIG. 7 is a diagram illustrating an example of a measurement result table.
FIG. 8 is a diagram illustrating an example of a weight table.

EMBODIMENTS

Mode for Carrying Out the Invention

An embodiment will hereinafter be described with reference to the drawings. A configuration of the embodiment is an exemplification, and a configuration of the invention is not limited to the specific configuration of the embodiment. On the occasion of carrying out the invention, specific configurations may be adopted corresponding to the embodiments.

Embodiment (Example of Configuration)

Figure 1:
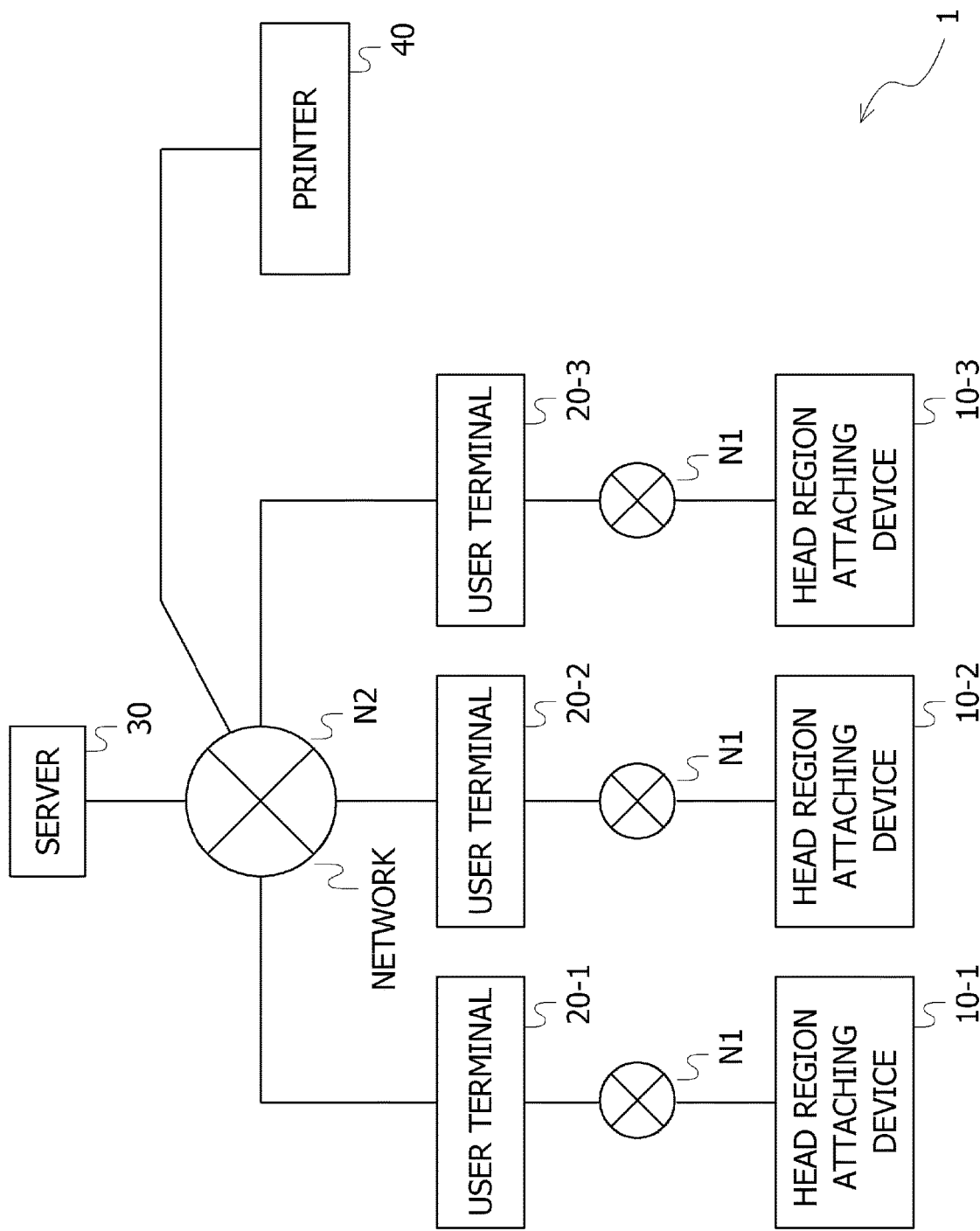
FIG. 1 is a diagram illustrating an example of a configuration of a selection system.

FIG. 1 is a diagram illustrating an example of a configuration of a selection system according to one embodiment of the present invention. A selection system 1 detects measurement data (also referred to as detection values) representing variations in bloodflow rate from a head region of a user performing a predetermined content, then acquires brain activity information (brain activity waveforms) indicating brain activity states of the user, and selects a proper content for training a brain of the user.

As in FIG. 1, the selection system 1 includes head region attaching devices 10-1, 10-2, 10-3, user terminals 20-1, 20-2, 20-3, a server 30, and a printer 40. Herein the head region attaching devices 10-1, 10-2, 10-3 are, when generically termed, referred to as the head region attaching devices 10. The user terminals 20-1, 20-2, 20-3 are, when generically termed, referred to as the user terminals 20. A number of the head region attaching devices 10 and a number of the user terminals 20 are not limited to "3", respectively. The printer 40 prints output results of the user terminals 20 onto a print sheet and other equivalent sheets. The printer 40 may be, though herein connected to a network N2, connected directly to the user terminals 20 and may also be connected to a network N1. The printer 40 may further be connected directly to the server 30. The printer 40 is one example of a "printing device". The server 30 may also be configured integrally with the user terminals 20.

Figure 2:
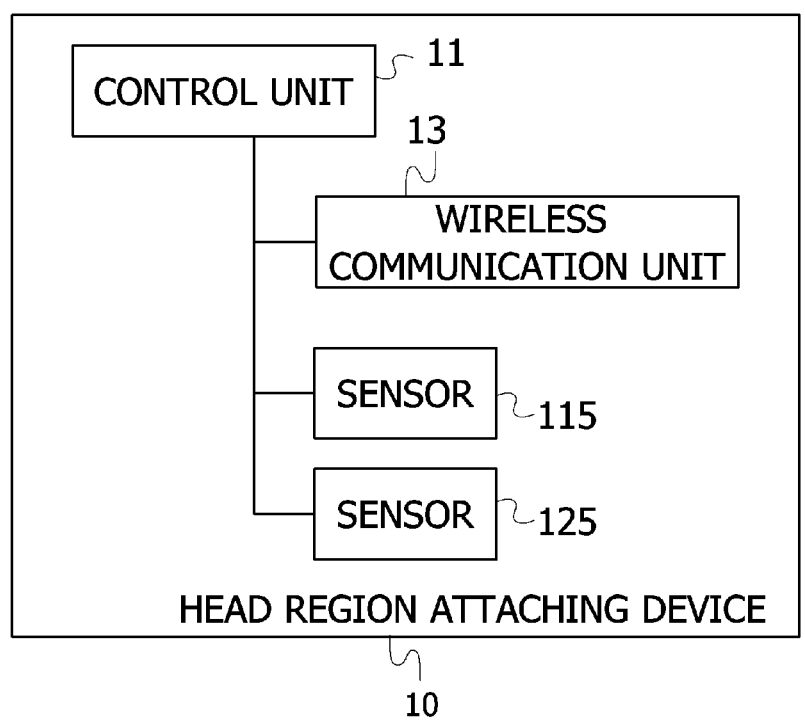
FIG. 2 is a diagram illustrating an example of a configuration of a head region attaching device.

FIG. 2 is a diagram illustrating an example of a configuration of the head region attaching device. The head region attaching device 10 includes, as an aspect of information processing, a control unit 11, a wireless communication unit 13, and a couple of sensors 115, 125. The control unit 11 controls measurements by and communications with the head region attaching device 10. The control unit 11 includes; e.g., a processor instanced by a CPU (Central Processing unit) or a DSP (Digital Signal Processor); and a memory, and executes processes based on a computer program, firmware and other equivalent software components deployed in an executable manner on the memory. However, the control unit 11 may also be a dedicated hardware circuit, an FPGA (Field Programmable Gate Array) and other equivalent elements that execute a cooperative process with each component by actuating the wireless communication unit 13 and the sensors 115, 125. The control unit 11 may also be configured as a mixture of the CPU, the DSP, the dedicated hardware circuit and other equivalent elements.

The head region attaching device 10 has a structure of being attached to a head region of a user by being wound on the head region in a headband-like shape, and fixed to the head region of the user by fastening a fixing member.

The wireless communication unit 13 is connected via a predetermined interface to the control unit 11, and the sensors 115, 125. However, the wireless communication unit 13 may be configured to acquire data from the sensors 115, 125 via the control unit 11. The wireless communication unit 13 performs the communications with the user terminal 20 via the network N1. The network N1 is a network pursuant to standards instanced by Bluetooth (registered trademark), wireless LAN (Local Area Network) and ZigBee (registered trademark). The wireless communication unit 13 is one example of "transfer means". It does not, however, mean that there is a limit to the standards of the wireless interface of the wireless communication unit 13 in the selection system 1.

When performing the communications via the network N1, an identifier for identifying the head region attaching device 10 is embedded into a header field of a communication header, or a user data field (payload field) of communication data, thereby enabling the user terminal 20 to identify the user (measurement examinee).

In the selection system 1, the wireless communication unit 13 maybe provided with a communication unit to perform wired communications in place of the wireless communication unit 13 or together with the wireless communication unit 13. In other words, the head region attaching device 10 may be connected to the user terminal 20 via an interface for the wired communications. It does not mean that there is a limit to the interface for the wired communications in this case; and a variety of interfaces instanced by USB (Universal Serial Bus) and PCI Express are, however, usable corresponding to applications of the selection system 1.

Each of the sensors 115, 125 receives near infrared-rays of light irradiated over the head region, partially absorbed and scattered in the vicinity of a cerebral cortex of a brain, and converts the scattered rays of light into electric signals. The cerebral cortex of the brain has different variations in bloodflow rate, e.g., depending on the brain activity states. As a result, there vary a quantity of haemoglobin bound to oxygen in the blood and a quantity of haemoglobin not bounded to oxygen in respective regions of the cerebral cortex. An absorptive characteristic or a scattering characteristic of the near infrared-rays of light in the vicinity of the cerebral cortex of the brain, varies due to variations in quantity of haemoglobin, variations in quantity of oxygen and other equivalent variations. Each of the sensors 115, 125 converts such near infrared-rays of light into the electric signals that a light quantity varies depending on variations in absorptivity or transmittance of the near infrared-rays of light in accordance with a state of the bloodflow in the vicinity of the cerebral cortex, and outputs the converted electric signals. The sensors 115, 125 are one example of "detection means".

Each of the sensors 115, 125 includes alight source for the near infrared-rays of light that irradiates the near infrared-rays of light, and a light receiving unit to receive the near infrared-rays of light. The light source of the near infrared-rays of light is instanced by an LED (Light Emitting Diodes) and an infrared-ray lamp. The light receiving unit includes: a photo-electric element instanced by a photo diode, and a photo transistor; an amplifier; and an AD (Analog-to-Digital) converter. Note that the light source for the near infrared-rays of light and the light receiving unit may be provided not to be paired. For example, a plurality of light receiving units may be provided for one light source the near infrared-rays of light.

Figure 3:
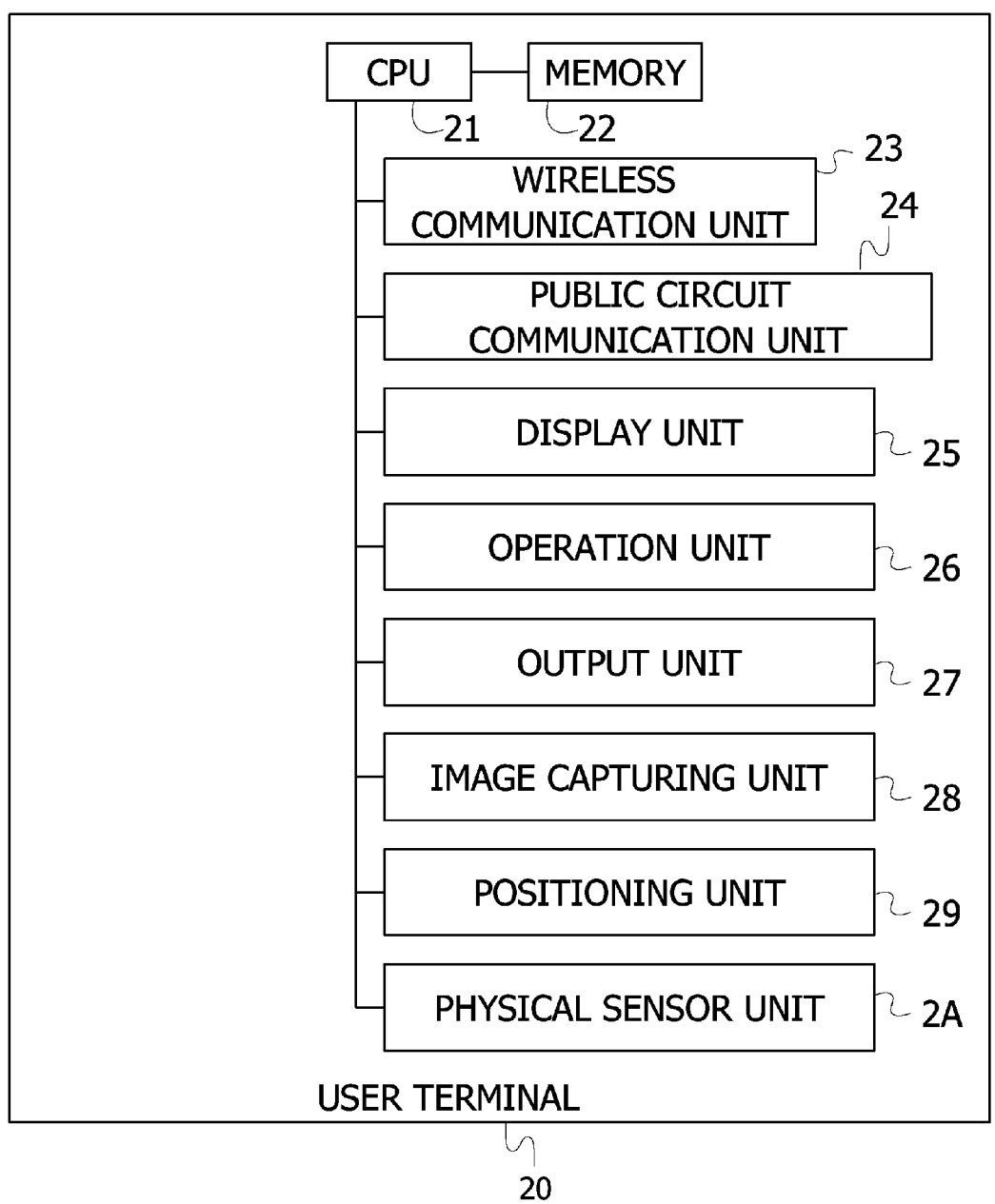
FIG. 3 is a diagram illustrating an example of a configuration of a user terminal.

FIG. 3 is a diagram illustrating an example of a configuration of a user terminal. A user terminal 20 acquires variation data of the absorptivity or transmittance of the near infrared-rays of light in the vicinity of the cerebral cortex of the user from the head region attaching device 10, and provides a service encompassing a variety of information processes pertaining to the brain activity states of the user. The user terminal 20 is one example of an "information processing apparatus (computer)". The user terminal 20 is attainable by using a dedicated or general-purpose computer instanced by a PC (Personal Computer), a smartphone, a mobile phone, a tablet terminal, a car navigation system and a PDA (Personal Digital Assistant), or an electronic equipment mounted with the computer. The user terminal 20 is installable in, e.g., a fitness club, a private cram school, and other equivalent facilities.

The user terminal 20 includes a CPU 21, a memory 22, a wireless communication unit 23, a public circuit communication unit 24, a display unit 25, an operation unit 26, an output unit 27, an image capturing unit 28, a positioning unit 29, and a physical sensor unit 2A. The CPU 21 executes processes as the user terminal 20, based on a computer program deployed in the executable manner on the memory 22. The processes as the user terminal 20 are defined as, e.g., the service encompassing the variety of information processes pertaining to the brain activity states of the user. The CPU 21, which runs such a computer program, is one example of "calculating means".

The memory 22 stores the computer program to be run by the CPU 21 or the data to be processed by the CPU 21. The memory 22 may include a volatile memory and a nonvolatile memory.

The wireless communication unit 23 is the same as the wireless communication unit 13 of the head region attaching device 10. The wireless communication unit 23 is one example of "receiving means". The user terminal 20 may include a communication unit to perform wired communications in place of the wireless communication unit 23 or together with the wireless communication unit 23.

The public circuit communication unit 24 performs the communications with a server, e.g., a server 30 and other equivalent apparatuses on a network N2 via this network N2. The network N2 is a public circuit network, e.g., a mobile phone network. The network N2 is the mobile phone network, in which case the public circuit communication unit 24 establishes a connection to the network N2 via a base station of the mobile phone network. However, the network N2 may also be a network including: an access network to a communication apparatus of an Internet provider; and the Internet. The access network to the communication apparatus of the Internet provider is instanced by an optical network and an ADSL (Asymmetric Digital Subscriber Line) provided by a common carrier. The network N2 is one example of a "public wireless network". The public circuit communication unit 24 is one example of "public wireless communication means". It does not, however, mean that the network N2 is limited to the public circuit network in the selection system 1; and the network N2 may also be an in-house network instanced by a LAN (Local Area Network), a private circuit of an enterprise, a business operator, a government office, a school, a research institute and other equivalent facilities, and a wide area network (WAN) instanced by a VPN (Virtual Private Network). The enterprise, the business operator, the government office, the school, the research institute and other equivalent facilities will hereinafter be simply termed the enterprise and other equivalent facilities.

The display unit 25 is instanced by a liquid crystal display and an EL (Electro-Luminescence) panel, and displays information outputted from the CPU 21. The operation unit 26 is instanced by a push button and a touch panel, and accepts user's operation. The output unit 27 is instanced by a vibrator to output vibrations and a loud speaker to output sounds or voices. The image capturing unit 28 is a camera including, a solid-state image capturing element. A CCD (Charge Coupled Device) image sensor, a CMOS (Complementary Metal Oxide Semiconductor) image sensor and other equivalent sensors are available as the solid-state image capturing element.

The positioning unit 29, which is, e.g., a GPS (Global Positioning System) receiver, calculates a present position (latitude, longitude, and other equivalent geographical coordinates) and the time by receiving radio waves from a GPS satellite. It does not, however, mean that the positioning unit 29 is limited to a unit having the GPS receiver. For example, the public circuit communication unit 24 is the mobile phone network, in which case the positioning unit 29 may execute positioning based on a distance from the mobile phone base station.

The physical sensor unit 2A is, e.g., an acceleration sensor or an angular acceleration sensor or other equivalent sensors. However, the physical sensor unit 2A may also be a temperature sensor, a humidity sensor, an atmospheric pressure sensor, or a water pressure sensor.

Figure 4:
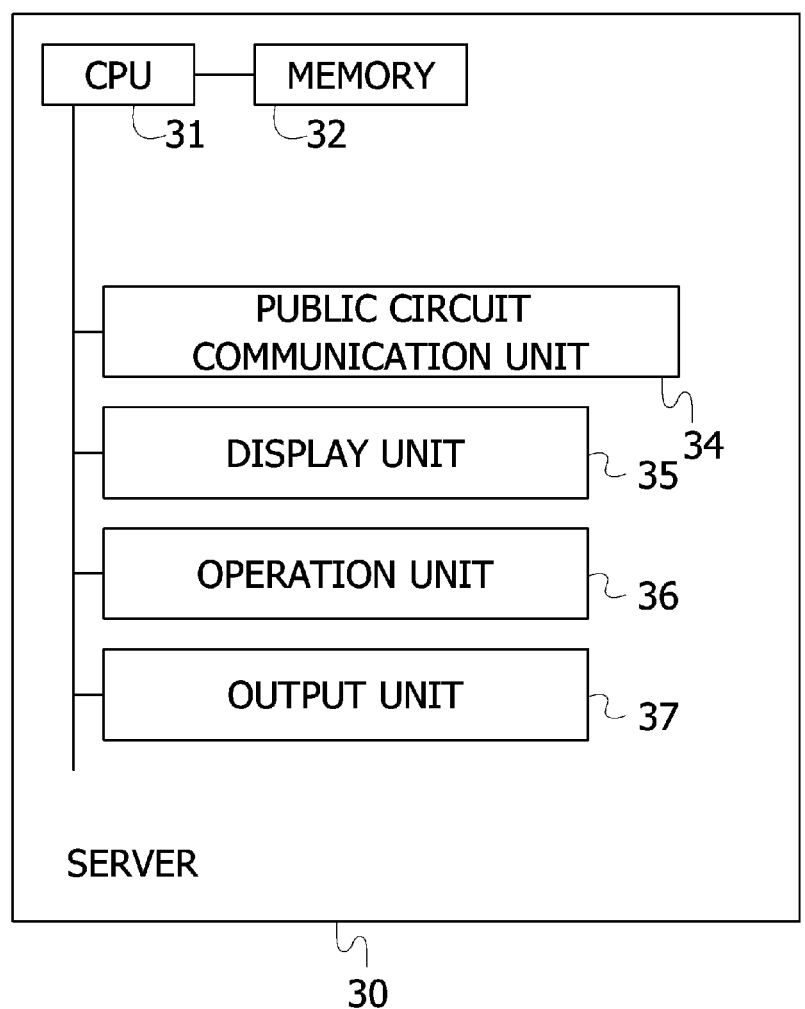
FIG. 4 is a diagram illustrating an example of a configuration of a server.

FIG. 4 is a diagram illustrating an example of a configuration of the server. The server 30 is connected to the network N2. The server 30 is a general information processing apparatus. The information processing apparatus includes: a CPU that executes an arithmetic operation and control; a memory and a storage unit that store the data and other equivalent information used for the arithmetic operation and other equivalent operations; an input unit that accepts inputting of information from the user and other equivalent persons; an output unit that outputs the information as images, voices and other equivalent elements, and a communication unit that transmits and receives the information to and from other apparatuses. The server 30 is attainable by using a dedicated or general-purpose computer instanced by the PC and a workstation (WS; Work Station), or an electronic equipment mounted with the computer.

The server 30 includes a CPU 31, a memory 32, a public circuit communication unit 34, a display unit 35, an operation unit 36, and an output unit 37. The CPU 31 executes processes as the server 30, based on a computer program deployed in the executable manner on the memory 32. The processes as the server 30 are defined as, e.g., a service encompassing the variety of information processes pertaining to the brain activity states. The CPU 31, which runs such a computer program, is one example of "calculating means".

The memory 32 stores the computer program to be run by the CPU 31, and the data to be processed by the CPU 31. The memory 32 may include the volatile memory and the nonvolatile memory. The memory 32 stores an individual information table T10 containing individual information of the users.

FIG. 5 is a diagram illustrating an example of the individual information table. The individual information table T10 in FIG. 5 stores items of individual information, i.e., an identifier (ID) of the user, a name, an address, a date of birth, a height, a weight, a distinction of sex, a disease (cerebral infarction, diabetes mellitus) previous illness and other equivalent information by being associated with each individual user.

The public circuit communication unit 34 performs the communications with apparatuses, e.g., the user terminals 20 on the network N2 via this network N2. The network N2 is the public circuit network, e.g., the mobile phone network. The public circuit communication unit 34 is one example of "public wireless communication means".

The display unit 35 is instanced by the liquid crystal display and the EL (Electro-Luminescence) panel, and displays information outputted from the CPU 31. The operation unit 36 is instanced by the push button and the touch panel, and accepts user's operation. The output unit 37 is instanced by the vibrator to output the vibrations and the loud speaker to output the sounds or the voices.

<Operational Example>

An operational example of the selection system of the embodiment will be described.

Figure 6:
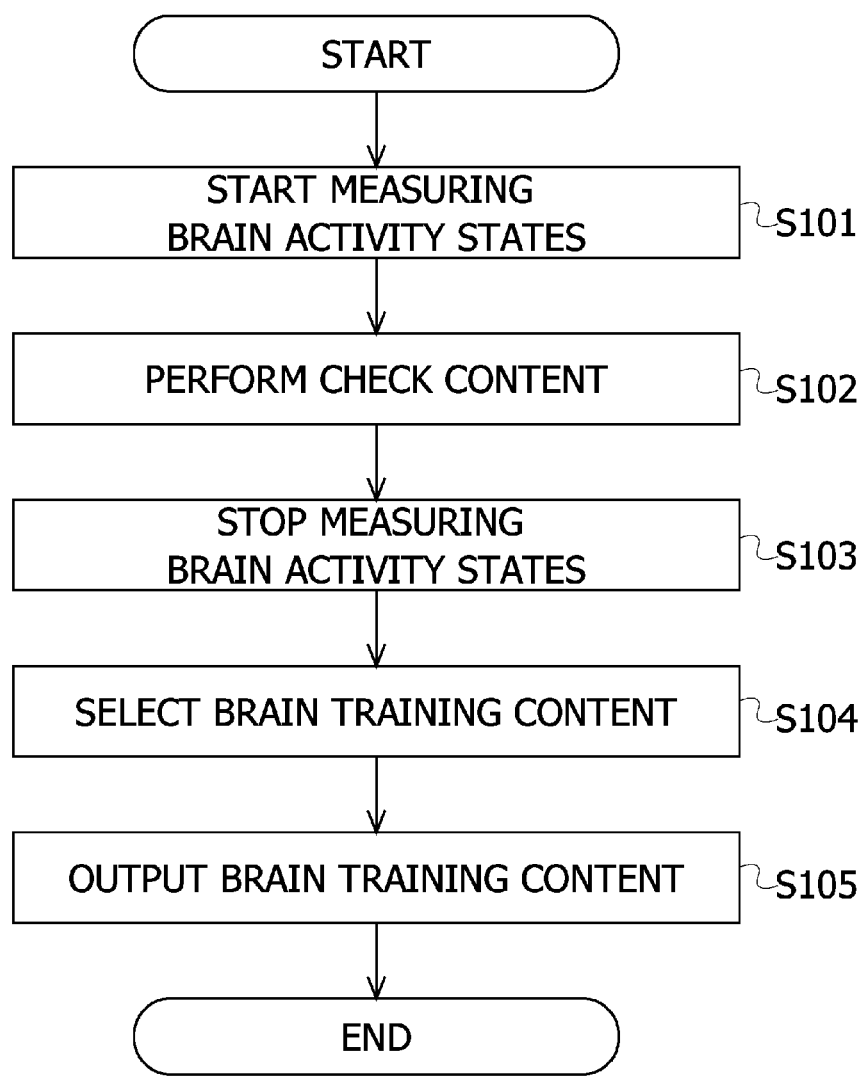
FIG. 6 is a flowchart illustrating an example of an operation flow of the selection system.

FIG. 6 is a flowchart illustrating an example of an operation flow of the selection system of the embodiment. Each head region attaching device 10 of the selection system 1 of the embodiment is in a status of being attached to the head region of the user (measurement examinee) and being enabled to measure the brain activity states (brain bloodflow rate). The respective head region attaching devices 10 are connected to the user terminals 20. An assumption is that calibration and other equivalent operations of the head region attaching device 10 are already done. It is also assumed that information about the measurement examinee is inputted to or selected in the user terminal 20, and the measurement examinee is specified. The user terminal 20 is connected to the server 30. The user terminal 20 is operated by the user or a trainer who trains the brain activity of the user.

In S101, the user terminal 20 causes the head region attaching device 10 to start measuring brain activity states of the user. The brain activity states are measured at a predetermined sampling frequency. Each head region attaching device 10 measures the brain activity states of the user with the aid of the sensors 115, 125, and transmits detection values representing the brain activity states to the user terminal 20 via the wireless communication unit 13. The user terminal 20, upon receiving the detection values (waveforms of the brain activities) indicating the brain activity states from the head region attaching device 10 via the wireless communication unit 23, stores the received detection values in storage means instanced by the memory 22. Herein, the detection value may be a measured value itself, and may also be information processed to facilitate transmission of the measured value to the user terminal 20, or may be information about an aggregation of the values measured for a fixed period. It may be sufficient that the detection value is a value based on the value obtained by the head region attaching device 10 that measures a variation in bloodflow of the head region the detection value may be a waveform of the brain activity and ma also be a brain activity value.

In S102, the user terminal 20 makes the user wearing the head region attaching device 10 perform a predetermined check content. The predetermined check content is exemplified by a power-of-memory test, an auditory test and a visual test. The user performs the content, which means that the user answers the tests. The predetermined check content may also be a specified behavior in a specified application. The respective check contents are contents enabling predetermined brain functions to be checked. One check content may be configured as a content enabling plural types of brain functions to be checked. The application includes, e.g., a brain training application. A unique identifier is previously allocated to each of the predetermined check contents. A unique identifier is also previously allocated to each individual user. For example, when conducting the power-of-memory test, the user terminal 20 causes the display unit 25 to display questions, and prompts the user to input answers to the questions on the operation unit 26. The user terminal 20 may make the user perform the tests in such a way that the printer 40 prints and thus outputs questions of a variety of tests. The user terminal 20 outputs signs of starting and finishing the predetermined behavior of the predetermined check content as images and voices through the display unit 25 and the output unit 27. The user terminal 20 may accept, through the operation unit 26, operation inputs of signs of starting and finishing a predetermined exercise (motion) of the predetermined check content. The user terminal 20 may allow the user to perform a plurality of predetermined check contents. When causing the user to perform the plurality of predetermined check contents, the user terminal 20 may stabilize the brain activity states of the user by providing a predetermined interval between the predetermined check content and the predetermined check content. This is to prevent the brain activity when conducting the previous check content from affecting the brain activity when conducting the later check content. The check contents are stored in the storage means instanced by the memory 22 of the user terminal 20. The user terminal 20 displays in real time the brain activity states of the user toward the trainer for the user, and the trainer may give an advice to activate the brain activity states of the user, while observing the brain activity states of the user. The user terminal 20 may also be configured in separation into a terminal for displaying the brain activity states and a terminal used for conducting the check content. This configuration enables the user to concentrate on conducting the check content.

In S103, the user terminal 20, upon an end of conducting the predetermined check content, causes the head region attaching device 10 to stop measuring the brain activity states of the user. The user terminal 20 stores the detection values indicating the brain activity states as, e.g., time-series data together with time information, the identifiers of the predetermined check contents and the identifiers of the users in the storage means instanced by the memory 22. The user terminal 20 invariably acquires the detection values indicating the brain activity states as measurement results, and may extract the detection values indicating the brain activity states while conducting the predetermined check content. The detection values (waveforms of the brain activity) are, e.g., time variations in brain bloodflow rate and time differentials of the brain bloodflow rates. The detection value may also be an average value of the brain bloodflow rates and an average value of the time differentials of the brain bloodflow rates. The detection value may also be a brain activity value. The brain activity value is calculated, e.g., as an amplitude width of the waveform of the brain activity (a difference between a maximum value and a minimum value), an integrated value of a variation quantity of the waveforms of the brain activity, a variation speed of the waveforms, and repetitive reproducibility of the waveforms of the brain activity. The brain activity value is a value indicating a degree of the brain activity, and represents that the brain gets energized more actively as the brain activity value is larger. The user terminal 20 may store the detection values indicating the brain activity states when conducting the check content in S102 on a user-by-user basis and on an every check-content basis in the storage means instanced by the memory 22. The user terminal 20 may store the detection values indicating the brain activity states when conducting the check content in S102 on the user-by-user basis and on an every brain-function basis in the storage means instanced by the memory 22. Here at, the detection values are separated per brain function, depending on the check contents.

FIG. 7 is a diagram illustrating an example of a measurement result table. A measurement result table T20 in FIG. 7 stores a user ID, names of the predetermined check contents, and detection values indicating the brain activity states with respect to the check contents by being associated with each other. The measurement result table T20 contains the user ID and the detection values indicating the brain activity states with respect to the plurality of predetermined check contents. Each measurement result may be associated with date/time of the measurement. For example, in (a record specified by) user ID "1001", a detection value "3" is stored in (a field of) a check content "visual", a detection value "1" is stored in (a field of) a check content "auditory", and a detection value "5" is stored in (a field of) a check content "short period memory". The names of the check contents maybe replaced by names of the brain functions. Herein, a high detection value in a certain check content represents that the brain function associated with the check content gets energized actively. The measurement result table T20 may store the test results (the result of the visual test, the result of the auditory test, and other equivalent test results) of the check contents by being associated with the respective detection values.

Herein, the brain activity is to include attributes of the visual function, the auditory function and the short-period memory. The brain activity may also include attributes of an exercise function and a long-period memory. The attributes of the brain activity are defined as natures, characteristics and features that are inherent in the brain activity. The attributes of the brain activity (brain activity attributes) are the attributes associated mainly with functions of a body. The visual function is a function to acquire visual information from eyes. The auditory function is a function to acquire acoustic information from ears. The exercise function is a function to move hands, feet and other equivalent regions. The short-period memory is memory retained for a period of several seconds through several tens of seconds after presenting a memorizing object. The long-period memory is memory retained for a period longer than the period retained in the short-period memory after presenting the memorizing object. Categories of the attributes of the brain activity are not limited to those described above, and the brain activity may include a much more types of attributes Each of the attributes of the brain activity may have an inherent brain activity waveform (basic waveform). To be specific, e.g., when the visual information is acquired from the eyes of the user (when the visual function is employed), the brain activity waveform is to include the brain activity waveform inherent in the visual function. Mathematically strict independency is not, however, indispensable for the basic waveform of each of the attributes of the brain activity. The brain activity waveform measured by the head region attaching device 10 is to be a sum of the basic waveforms of the respective attributes of the brain activity. A size of the basic waveform of the brain activity, which is contained in the brain activity waveform, depends on a size corresponding to an extent of how much the respective attributes of the brain activity are used.

The server 30 may preset, for the respective predetermined check contents, the brain activity waveforms presumed when the users perform the predetermined check contents. The brain activity waveform to be set is expressed as a sum of the inherent brain activity waveforms of the respective attributes of the brain activity. A brain activity waveform Sapp1 set for a certain single predetermined check content (app1) is expressed, e.g., as follows:

[Mathematical Expression 1]

-continued $$S_{app1} = (M_{a1}\ M_{b1}\ M_{c1}\ M_{d1}\ M_{e1})(X_a\ X_b\ X_c\ X_d\ X_e)^T \quad (1)$$
$$= M_{a1}X_1 + M_{b1}X_b + M_{c1}X_c + M_{d1}X_d + M_{e1}X_e$$

where, $X_a$ is the inherent brain activity waveform (basic waveform) of the visual function defined as one of the attributes of the brain activity, $X_b$ is the basic waveform of the auditory function, $X_c$ is the basic waveform of the exercise function, $X_d$ is the basic waveform of the short-period memory function, and $X_e$ is the basic waveform of the long-period memory function. Further, $M_{a1}$ is a weight (attribute value) of the visual function for the check content (app1), $M_{b1}$ is a weight of the auditory function for the check content, $M_{c1}$ is a weight of the exercise function for the check content, $M_{d1}$ is a weight of the short-period memory function for the check content, and $M_{e1}$ is a weight of the long-period memory function for the check content. The attribute weight of the brain activity for the check content is a quantity indicating a magnitude of the brain activity, which is expected with respect to this attribute. The attribute weight of the brain activity for the check content represents a tendency of the brain activity state about the check content. This implies that as the attribute weight (attribute value) of a certain brain activity in a certain check content is larger, the attribute function of the brain activity works more actively when conducting the check content. The respective attribute weights are preset by tools supporting a maker of the check contents, or by a designer of test questions, application programs and other equivalent tests. The same is applied to brain training contents that will be described later. These tools, application programs and other equivalent tests are provided by the user terminal 20 and other control devices.

The user terminal 20 transmits the detection values indicating the brain activity states, which are stored in the storage means, together with the identifiers of the check contents (brain functions), the identifiers of the users, the time information and other equivalent items to the server 30 via the public circuit communication unit 24. The user terminal 20 may also transmit the measurement result table T20 to the server 30.

The server 30 receives the detection values indicating the brain activity states, the identifiers of the check contents (brain functions), the identifiers of the users, the time information and other equivalent items from the respective user terminals 20 via the public circuit communication unit 34. The server 30 stores the received detection values indicating the brain activity states in the memory 32 by being associated with the identifiers (IDs) of the predetermined check contents (brain functions), the identifiers (IDs) of the users, the time information and other equivalent items. The detection values given when the various users perform the variety of predetermined check contents are accumulated in the memory 32 of the server 30. The server may store the detection values, the identifiers of the predetermined check contents (brain functions), the start time of each of the check contents, the end time of each of the check contents, and the identifiers of the users performing the check contents by being associated with each other in the memory 32. It may be sufficient that the detection values and other equivalent items are stored in the memory 32 of the server 30 in order to enable the specified user to extract the detection values when performing the specified check content.

In S104, the server 30 selects the brain training content proper for the user to activate the brain activity, based on the detection values and other equivalent items indicating the brain activity states for the respective check contents. The brain training contents are the power-of-memory test, the auditory test, the visual test, watching videos, play of games, music appreciation, exercises, eating and drinking, meditation, sleep, yoga, and play of applications. A meaning that the user performs the brain training content is that the user makes answers to the tests, appreciates the music, and plays the applications. The brain training content may also be a specified behavior in the specified application. The application includes, e.g., a brain training application. The attribute weights of the brain activity for the brain training content are stored as a weight table T30 in the memory 32 of the server 30.

FIG. 8 is a diagram illustrating an example of the weight table. The weight table T30 in FIG. 7 stores names of the brain training contents and the weights (attribute values) of the check contents (brain functions) by being associated with each other. The weight table T30 contains the weights of the respective check contents with respect to the plurality of brain training contents. For example, in (a record specified by) a content name "content A" for the brain training, a weight (attribute value) "3" is stored in (a field of) a check content "visual", a weight "0 is stored in (a field of) a check content "auditory", and a weight "2" is stored in (a field of) a check content "short-period memory". The weights of the check contents associated with the brain functions actively working are contrived to increase when performing the brain training contents.

The server 30 compares the detection value as the measurement result per check content of the user with the weight per check content of each brain training content, and selects the brain training content exhibiting a high correlation from the weight table T30. The brain activity states of the user change at all times due to influence caused by stimuli from outside, and hence it is not necessarily feasible to measure the brain activity states from the same brain activity states every day. For example, when something good to the user happens until immediately before the measurement on a very measuring day, the brain activity state on that day works actively as the case may be. Therefore, even when setting the questions of the same level, a percentage of correct answers may differ. The daily measurements of the brain activity states by using the check contents perform an important role in terms of activating the brain activity of the user. A magnitude of the correlation is expressed by a magnitude of a sum of squares of differences between the detection values of the check contents and the weights. The correlation becomes higher as the sum becomes smaller. The sum and the weight may be respectively standardized beforehand. The magnitude of the correlation may be calculated by other methods. The server 30 is thereby enabled to select the brain training content that more activates the brain activity of the user. The server 30 may also select the brain training content exhibiting a low correlation. The server 30 is thereby enabled to select the brain training content for training the brain function with the user's brain activity being inactive. The server 30 may select the brain training content exhibiting a high weight of the brain function associated with the check content exhibiting a low percentage of correct answers to the tests for the user. The server is thereby enabled to select the brain training content pertaining to the brain function, with the brain activity being active, exhibiting the low percentage of correct answers to the tests. The server 30 notifies the user terminal 20 of the information of the selected brain training content.

A method of how a level (a degree of difficulty) of the brain training content to be selected from the user is determined, will be described. When consecutively providing the brain training contents having the same level, the percentage of correct answers is not always improved. When providing combinations of the brain training contents of different levels, differences occur in the percentage of correct answers and in the brain activity between the brain training contents having the same level in some cases. Herein, a focus is put on when the brain activity of the user does not work actively. When the percentage of correct answers decreases due to a decline of the brain activity, the user feels level-difficulty of this brain training content, and judges that the brain activity lowers. In this case, the level of the brain training content is lowered one by one. The brain activity declines, and nevertheless, when the percentage of correct answers increases, it follows that the user feels level-easiness of this brain training content and judges that the brain activity lowers (rises). In this case, the level of the brain training content is raised by one. Conversely when the brain activity works more actively, it is determined that the user has an interest in the provided brain training content irrespective of the percentage of correct answers rising or lowering, and the level of the brain training content continues to be kept.

In S105, the user terminal 20 receives the information of the selected brain training content from the server 30. The user terminal 20 prints the selected brain training content onto the print sheet and outputs the sheet by using the printer 40. The user terminal 20 outputs questions of the various categories of tests of the selected brain training content, and makes the user perform the tests. The user brings back the questions of the printed tests and is thus enabled to carry out the brain training content even when not having the user terminal 20. The user terminal 20 may print the detection values indicating the brain activity states of the user onto the print sheet and may output the sheet by use of the printer 40. Hereat, the user terminal 20 may output the detection value measured finally together with the past detection values. The user compares the past detection values with the detection value measured finally, and is thereby enabled to check outcomes by the brain training. The output may include the percentage of correct answers to the tests in the brain training content. The brain training content is stored in the storage means instanced by the memory 22 of the user terminal 20.

The user terminal 20 causes the display unit 25 to display the questions when making the user perform the power-of-memory test as the brain training content, and may make the user input answers to the questions through the operation unit 26. The user terminal 20 causes the display unit 25 to display a video when making the user watch and listen to the video, and causes the output unit 27 to output sounds and voices of the video, thus making the user watch and listen to the video. The user terminal 20 causes the display unit 25 and the output unit 27 to output pictures and sounds/voices for a game when making the user play the game, and makes the user operate the game through the operation unit 26, thus making the user play the game.

The server 30 calculates the detection value (brain activity value) per attribute of the user, and may notify the user terminal 20 of the calculated detection value. For example, on the occasion of calculating the brain activity values given when males aged over 20 years conduct the predetermined check content "auditory", the server 30 extracts the brain activity waveforms of the predetermined check content "auditory", further extracts the males aged over 20 years from within the users associated with these brain activity waveforms by referring to the individual information table T10 and other equivalent tables, and calculates the brain activity values by using the brain activity waveforms of the extracted users. With this contrivance, it is feasible to calculate the brain activity values under the specified condition and a distribution of the brain activity values. The server 30 stores, in the memory 32, the calculated brain activity values and the calculated distribution of the brain activity values. The server 30 transmits the brain activity values and the distribution of the brain activity values, which are stored in the memory 32, to the user terminal 20. The user terminal 20 displays the received brain activity values and the received distribution of the brain activity values through the display unit 25 and/or the display means of the output unit 27, and outputs a print by printing these values and the distribution through the printer 40. The user is enabled to compare the self detection values with the detection values of other users having the similar attributes as those of the self user. The user is also enabled to grasp a self rank order among the whole users. The user is further enabled to check the current brain activity states in comparison with the past self brain activity states by comparing the past self detection values given when the same user performs the same check content with the current self detection values.

The embodiment may be carried out by combining the configurations of the embodiments to the greatest possible degree.

(Operation and Effect of Embodiment)

In the selection system according to the embodiment, the user terminal 20 causes the head region attaching device 10 to measure the brain activity states when making the user conduct the predetermined check content. The server 30 acquires the brain activity states transmitted from the user terminal 20. The server 30 selects a more proper brain training content, based on the measured brain activity states. The user terminal 20 prints the questions of the test for the selected brain training content onto the print sheet and outputs the sheet by using the printer 40.

The selection system according to the embodiment enables the proper brain training content to be selected based on the brain activity values given when performing the check content.

BRIEF DESCRIPTION OF THE REFERENCE NUMERALS AND SYMBOLS 10 head region attaching device
11 control unit
13 wireless communication unit
115 sensor
125 sensor
20 user terminal
21 CPU
22 memory
23 wireless communication unit
24 public circuit communication unit
25 display unit
26 operation unit
27 output unit
28 image capturing unit
29 positioning unit
2A physical sensor unit
30 server
31 CPU
32 memory
34 public circuit communication unit
35 display unit
36 operation unit
37 output unit
40 printer

What is claimed is:

1. A system comprising:
a head region attaching device including a plurality of sensors, each of the sensors converting near infrared rays of light into electrical signals based on a measured blood flow rate in a brain of a user while the user performs a predetermined check content, the head region attaching device transmitting a plurality of detection values based on the measured blood flow rate;
a storage configured to store the plurality of the detection values indicating the measured blood flow rate, an identifier of the predetermined check content to be performed by the user when detecting the detection value, and an identifier of the user by being associated with each other; and
a processor configured to:
calculate a brain activity value representing a degree of a brain activity state of the user when making the user perform the predetermined check content, based on the detection value stored in the storage;
change, when the brain activity value lowers, a level of a brain training content being performed by the user, based on a percentage of correct answers of the user when making the user perform the predetermined check content calculated by the processor, and maintain, when the brain activity value rises, the level of the brain training content irrespective of the percentage of correct answers; and
a display configured to display the brain training content, wherein the processor is further configured control the display to display the changed or maintained brain training content.

2. The system according to claim 1, wherein the processor is configured to vary a level of the brain training content when the user's brain activity value calculated by the processor decreases.

3. The system according to claim 1, further comprising a printer configured to output the brain training content selected by the processor onto a print sheet.

4. The system according to claim 3, wherein the printer is configured to output the brain activity value calculated by the processor onto the print sheet.

5. A method comprising the steps of:
converting by a plurality of sensors, in a head region attaching device, near infrared rays of light into electrical signals based on a measured blood flow rate in a brain of a user while the user performs a predetermined check content,
transmitting, by the head region attaching device, a plurality of detection values based on the measured blood flow rate;
storing, in a memory, the plurality of the detection values indicating the measured blood flow rate, an identifier of the predetermined check content to be performed by the user when detecting the detection value, and an identifier of the user by being associated with each other;
calculating, using a processor, a brain activity value representing a degree of a brain activity state of a user when making the user perform a predetermined check content, based on a detection value given by detecting a blood flow rate of a head region of the user and associated with both an identifier of a predetermined check content to be performed by the user when detecting the detection value and an identifier of the user;

changing, using the processor, when the brain activity value lowers, a level of a brain training content being performed by the user, based on a percentage of correct answers of the user when making the user perform the predetermined check content, and maintain, when the brain activity value rises, the level of the brain training content irrespective of the percentage of correct answers; and displaying, using a display, the changed or maintained brain training content.

6. A non-transitory computer readable medium storing a program for making a computer execute:

storing, in a memory, a plurality of detection values indicating a measured blood flow rate while the user performs a predetermined check content value, an identifier of the predetermined check content to be performed by the user when detecting the detection value, and an identifier of the user by being associated with each other, the detection values be calculated based on the measured blood flow rate by converting by a plurality of sensors, in a head region attaching device, near infrared rays of light into electrical signals based on the measured blood flow rate in a brain of a user;

calculating, using a processor, a brain activity value representing a degree of a brain activity state of a user when making the user perform a predetermined check content, based on a detection value given by detecting a blood flow rate of a head region of the user and associated with both an identifier of a predetermined check content to be performed by the user when detecting the detection value and an identifier of the user;

changing, using the processor, when the brain activity value lowers, a level of a brain training content being performed by the user, based on a percentage of correct answers of the user when making the user perform the predetermined check content, and maintain, when the brain activity value rises, the level of the brain training content irrespective of the percentage of correct answers; and displaying, using a display, the changed or maintained brain training content.

* * * * *